(12) United States Patent　　(10) Patent No.: US 7,405,222 B2
Sallis et al.　　(45) Date of Patent: Jul. 29, 2008

(54) METHODS AND COMPOSITIONS FOR TREATMENT OF ERECTILE DYSFUNCTION

(75) Inventors: Ramsey Sallis, St. Peters (AU); Quoc Huan Ha, Irvine, CA (US)

(73) Assignee: Modular Properties, Ltd., Altamonte Springs, FL (US)

( * ) Notice: Subject to any disclaimer, the term of this patent is extended or adjusted under 35 U.S.C. 154(b) by 285 days.

(21) Appl. No.: 10/351,049

(22) Filed: Jan. 24, 2003

(65) Prior Publication Data

US 2003/0144318 A1　Jul. 31, 2003

Related U.S. Application Data

(60) Provisional application No. 60/351,634, filed on Jan. 25, 2002.

(51) Int. Cl.
　　*A61K 31/505*　(2006.01)
　　*A61K 31/415*　(2006.01)
　　*A61K 31/19*　(2006.01)
　　*A61K 31/557*　(2006.01)
　　*A61K 31/445*　(2006.01)

(52) U.S. Cl. ................. 514/273; 514/396; 514/573; 514/319

(58) Field of Classification Search ............ 514/273, 514/319, 396, 573
See application file for complete search history.

(56) References Cited

U.S. PATENT DOCUMENTS

| | | | | |
|---|---|---|---|---|
| 4,127,118 A | | 11/1978 | Latorre | 600/38 |
| 5,145,852 A | * | 9/1992 | Virag | 514/252.14 |
| 5,256,652 A | * | 10/1993 | El-Rashidy | 514/58 |
| 6,127,363 A | * | 10/2000 | Doherty et al. | 514/220 |
| 6,200,591 B1 | | 3/2001 | Hussain et al. | 424/434 |
| 6,300,335 B1 | | 10/2001 | Campbell et al. | 514/260 |
| 6,303,135 B1 | | 10/2001 | Cutler | 424/423 |
| 6,323,211 B1 | | 11/2001 | Garvey et al. | 514/280 |
| 6,323,241 B1 | | 11/2001 | Yeager et al. | 514/573 |
| 6,333,330 B1 | | 12/2001 | Bunnage et al. | 514/258 |

OTHER PUBLICATIONS

Abbott and Hirsch, International Journal of Impotence Research, 1997;9:39-42.*

Harrison's Principles of Internal Medicines, 13th ed., 1994, pp. 263-265.*

Bechara, A, Casabe A, Cheliz, G, Romano S and Fredotovich N., Prostagladin E1 Versus Mixture of Prostagladin E1, Papaverine and Phentolamine in Nonresponders to High Papaverine Plus Phentolamine Doses, *The Journal of Urology*, vol. 155(3), 913-914. (Mar. 1996).

Truss et al., "Intracavernous pharmacotherapy," Abstract, World Journal of Urology, 15:71-77, 1997.

(Continued)

*Primary Examiner*—San-ming Hui
(74) *Attorney, Agent, or Firm*—Baker & Hostetler LLP

(57) ABSTRACT

Disclosed are methods and compositions for treatment of male sexual dysfunction. A method of treating male sexual dysfunction includes administering a pharmaceutical composition effective to cause said male to sustain an erection. The composition is formulated based on diagnostic assessment and an individualized formulation test step. Also within the invention is a method of treating male sexual dysfunction in a population of subjects. The invention further provides kits for treatment of male erectile dysfunction.

36 Claims, 2 Drawing Sheets

CHART 1

SCHEME FOR FIRST TEST DOSE

| | Group 1 | Group 2 | | Group 3 | | Group 4 | |
|---|---|---|---|---|---|---|---|
| | Blood flow >20cm/s<br>Erection 100%<br>PE<br>Neurogenic ED<br>Psychogenic ED | Blood flow 15-20cm/s<br>Erection >70-75%<br>Sustain Poor<br>Morning<br>Erection OK<br>Dysfunction <12 Months<br>Penetration >50% of the time<br>Sildenafil Worked Well | | Blood flow 10-15cm/s<br>Erection <65%<br>Sustain Poor<br>Morn. Erect Poor<br>Dysfunction 12-24 Mo.<br>Penetration 50% of time | | Blood flow <10cm/s<br>Erection <50% ± Diabetes<br>Sustain Poor<br>Morn. Erect. Poor<br>Dysfunction >24 Months<br>Penetration Not Possible | |
| AGE | F1 | F1 | F2 | F2 | | F2 | |
| 20-30 | 10 | 18 | - | 14 | | 20 | |
| 30-40 | 14 | 24 | - | 20 | | 26 | |
| 40-50 | 16 | 34 | - | 26 | | 30 | |
| 50-60 | 18 | - | 20 | 30 | | 36 | |
| 60-70 | 20 | - | 24 | 36 | | 40 | |
| 70+ | 22 | - | 26 | 40 | | 50 | |

OTHER PUBLICATIONS

Lue et al., "Functional evaluation of penile arteries with duplex ultrasound in vasodilator-induced erection," Abstract, Urological Clinics of North America, 16:799-807, 1989.

Supplemental Partial Search Report, dated Mar. 17, 2005 (attached to Communication from the European Patent Office, dated Mar. 30, 2005).

"Three-Year Outcome of a Progressive Treatment Program for Erectile Dysfunction with Intracavernous Injections of Vasoactive Drugs," J. Baniel, et al., *Urology*, 56 (4), 2000.

"Clinical Reliability of Multi-Drug Intracavernous Vasoactive Pharmacotherapy for Diabetic Impotence," F. Montorsi, et al., *Acta Diabetol*, 31:1-5, 1994.

"Effectiveness and Safety of Multidrug Intracavernous Therapy for Vasculogenic Impotence," F. Montorsi, et al., *Urology*, vol. 42, No. 5, Nov. 1993.

"Progressive Treatment of Erectile Dysfunction with Intracorporeal Injections of Different Combinations of Vasoactive Agents," J. Shmueli, et al., International Journal of Impotence Research, 11, 15-19, (1999).

\* cited by examiner

CHART 1

| SCHEME FOR FIRST TEST DOSE | Group 1 | | Group 2 | | Group 3 | | Group 4 | |
|---|---|---|---|---|---|---|---|---|
| | Blood flow | >20cm/s | Blood flow | 15-20cm/s | Blood flow | 10-15cm/s | Blood flow | <10cm/s |
| | Erection | 100% | Erection | >70-75% | Erection | <65% | Erection | <50% ± Diabetes |
| | PE | | | | | | | |
| | Neurogenic ED | | Sustain | Poor | Sustain | Poor | Sustain | Poor |
| | Psychogenic ED | | Morning Erection | OK | Morn. Erect. | Poor | Morn. Erect. | Poor |
| | | | Dysfunction | <12 Months | Dysfunction | 12-24 Mo. | Dysfunction | >24 Months |
| | | | Penetration | >50% of the time | Penetration | 50% of time | Penetration | Not Possible |
| | | | Sildenafil | Worked Well | | | | |
| AGE | F1 | | F1 | | F2 | | F2 | |
| 20-30 | 10 | | 18 | | 14 | | 20 | |
| 30-40 | 14 | | 24 | | 20 | | 26 | |
| 40-50 | 16 | | 34 | | 26 | | 30 | |
| 50-60 | 18 | | - | | 30 | | 36 | |
| 60-70 | 20 | | 24 | | 36 | | 40 | |
| 70+ | 22 | | 26 | | 40 | | 50 | |

FIG. 1

CHART 2

| SUGGESTED PRESCRIPTION FOR ED | | | SUGGESTED PRESCRIPTION PER PE | |
|---|---|---|---|---|
| Erection Not Rigid<br><br>Cannot Penetrate | Erection 50-70%<br><br>Firm & Rubbery<br><br>Just Able to Penetrate | Erection 70-80%<br><br>Reasonably Firm<br><br>Penetration Reasonably Easy | Erect. <50%<br><br>Not Firm | Erection 70%<br><br>Firm & Rubbery |
| Double | + 50-75% | + 25 – 50% | + 50% | Same Dose |

- If patient has a priapism, or 100% response for 3-6 hours which reduces with conservative treatment or epinephrine, change F2 to F1 or F1 to F0.

- If patient has a priapism that requires draining, start with 20F0.

- F5 is high potency F2. If 100F2 fails, use 100F5.

- F4 does not need refrigeration. Start with 75% of the volume appropriate for F2.

- F6 is diluted F4 (i.e., non-refrigerated), for use with PE patients. Start with 14F6.

FIG. 2

METHODS AND COMPOSITIONS FOR TREATMENT OF ERECTILE DYSFUNCTION

CROSS REFERENCE TO RELATED APPLICATIONS

This application claims priority from U.S. Provisional Application Ser. No. 60/351,634 filed Jan. 25, 2002. The foregoing is herein incorporated by reference.

FIELD OF THE INVENTION

This invention relates generally to the fields of medicine and urology. More particularly, the invention relates to methods and compositions for treatment of male erectile dysfunction.

BACKGROUND OF THE INVENTION

Sexual dysfunction in both males and females has received a significant amount of popular attention with the greater concerns directed to the particular male problems of erectile capacity and penetration ability. Male sexual dysfunction associated with impotence is generally defined as the inability to attain or sustain an erection satisfactory for normal coitus. Prevalence of erectile problems, including premature ejaculation, has been estimated to be surprisingly high, perhaps as much as 45% worldwide. This is a particular concern among the over-50 male population in the United States, where estimates of impotency range from 18 to 75% for this age group.

Medical intervention for treatment of erectile dysfunction is becoming increasingly common. Surgical procedures, penile implants and pharmacological agents have been developed for treatment of male erectile dysfunction in recent years.

Surgical interventions employing penile implants and various patient-controlled mechanical devices are not uniformly successful nor are they appropriate in most situations. A serious disadvantage of treating erectile dysfunction with a surgical implant is the necessity to irreversibly damage the erectile tissues of the penis.

Pharmacological methods have been developed to treat male erectile dysfunction. The mechanism of erection is dependent on adequate blood flow to the spongy cavernous tissue of the penis, in paired spaces known as the corpora cavernosa. Control of blood flow to the corpora cavernosa involves the process of vasodilation of the cavernosal arteries.

It is now recognized that vasodilators acting on the penile arteries can be beneficial to achieving an erection. Orally administered vasodilators are currently the most widely accepted treatments for male erectile dysfunction. Such vasodilators include sildenafil. This compound is taken orally about one hour prior to intercourse because instant erection is not achieved with this drug. Unfortunately, this delay may lead to overdosing by patients seeking a more rapid response. While effective, this product may cause undesirable side effects such as headache, flushing, dyspepsia and in some cases abnormal vision such as increased sensitivity to light. Of greater concern, this drug may exacerbate pre-existing heart conditions. Furthermore, sildenafil must be taken on an empty stomach and must not be taken with alcohol.

A more rapid response in producing an erection has been found for sildenafil applied intranasally. The response is often within five minutes, and the drug is asserted to have fewer side effects than when administered orally. While reducing side effects, the drug nevertheless enters the circulatory system and is able to exert vasodilatory effects in areas other than the penis. Following the nasal route of administration, undesirable side effects can still be produced, some of which may be of medical concern.

Recognition of the problems associated with systemic administration of vasodilators has led to development of methods for local delivery of vasodilators to the tissues of the penis. For example, a semi-solid vehicle containing a vasodilator for insertion into the urethra has been formulated and shown to be effective in stimulating erection. Disadvantages of this method are the requirement for administration into the urethra, contributing to transient burning or tingling effects reported in some cases, and raising the possibility of urethral infection and scarring. This product is ineffective in up to 60% of patients.

An alternative and more direct route for delivery of vasodilators is injection into the corpus cavernosum of the penis. This "intracavernosal" route has been successfully used to deliver one or more vasodilators to achieve erections, and has led to the development of a treatment regimen known as intracavernosal pharmacotherapy (ICP).

Studies have led to the discovery of several vasodilators capable of provoking an erection. The use of papaverine for male erectile dysfunction has been reported. Papaverine is a vascular intracellular smooth muscle relaxant acting by its inhibitory effect on cyclic mononucleotide phosphodiesterases. However papaverine as monotherapy had an unpredictable response, and the drug must be administered in large volumes. Additionally, significant side effects associated with papaverine include the potential for prolonged erection and fibrosis of the corpus cavernosum.

Another vasodilator that has been used to achieve erection is phentolamine. Phentolamine alone does not reliably produce an erection sufficient for intercourse.

Prostaglandin E1 (PGE1) is a yet another vasodilator that effects an erection through its action as an alpha-adrenergic blocker. PGE1 has been formulated into suppositories for insertion into the urethra of men suffering from erectile dysfunction. As described above, this method of administration is disadvantageous due to risk of urethral infection and fibrosis. PGE1 has a short half life compared with papaverine and phentolamine. Intracavernosal injection of PGE1 can cause an erection of dose-dependent duration but, in a trial of this method, was associated with significant pain in a large percentage (up to 40%) of the subjects.

Several combinations of vasodilators have been used for treatment of impotence by the intracavernosal route. Success has been reported in a clinical study using a combination of papaverine and phentolamine in patients having vascular causes of impotence mostly associated with diabetes or atherosclerosis. Clinical success has also been reported in men with erectile dysfunction of neurogenic origin using a combination of papaverine, phentolamine and PGE1. The three-drug mixture has been regarded as more effective than PGE1 alone in inducing an erectile response, with a decreased incidence of pain. This drug combination also decreases the latency between injection and erection and allows a reduction in the total papaverine dose, reducing the risk of prolonged erection and potential incidence of fibrosis.

The collective experience of urologists reviewing clinical trials and treating patients with erectile dysfunction has led to an appreciation that despite impressive successes with some patients, no one therapy or composition can be applied across-the-board to treat all erectile problems.

SUMMARY

The invention provides a method of treating sexual dysfunction in a male mammal that includes administering by ICP a pharmaceutical composition of one or more agents in an amount effective to cause the male to sustain an erection. The method includes the steps of: a) assessing the general, physical and psychological condition of the male; b) formulating a test dose of the composition guided by step a); c) administering a test dose; d) observing at least one erection characteristic of the male subsequent to administration of the test dose; and e) adjusting the composition to provide an effective erection.

Assessment of the physical condition can include measuring blood flow to the arteries of the penis. The physical assessment can also include determining the sensitivity and condition of the nerves of the penis.

The nature of the sexual dysfunction treatable by the method can be erectile dysfunction. Premature ejaculation can also be treated.

The compositions used in the method can include at least one vasodilator. At least one vasodilator of the compositions can be PGE1, papaverine, phentolamine, or atropine. The compositions can include PGE1, papaverine, phentolamine, and atropine. In general, the respective amounts of PGE1, papaverine, phentolamine, and atropine can range from about 8-35 µM, 14-45 mM, 2-15 mM and 0.05-0.15 mM.

The relative amounts of the vasodilators can be varied in different formulations of the compositions. This is advantageous for preparation of customized formulations tailored to individual patient needs, e.g., in a clinical setting. In one embodiment, the composition can include respective amounts of PGE1, papaverine, phentolamine and atropine of about 3 µg, 13.5 mg, 2.5 mg, and 0.15 mg in a volume of 1 ml. In other embodiments, the respective amounts can be about 6 µg, 10.5 mg, 2 mg, and 0.15 mg. In yet other embodiments, the respective amounts can be about 12 µg, 6 mg, 2.5 mg and 0.05 mg; 12 µg, 21 mg, 4 mg, and 0.3 mg; or 3 µg, 5 mg, 1 mg and 0.8 mg in a volume of 1 ml. In general, preferred embodiments of the compositions can range in amounts from about 3-12 µg/ml PGE1, 5-15 mg/ml papaverine, 1-5 mg/ml phentolamine, and 0.5-0.15 mg/ml. In yet a further embodiment, the composition can include papaverine, phentolamine, and atropine in amounts of about 12 µg, 4 mg and 0.2 mg in a volume of 1 ml.

The composition used in the method can be in a pharmaceutically acceptable vehicle. The vehicle can further include a stabilizer.

The effective amount of a composition used in the method of treatment can be contained in a volume from about 0.1 ml to about 2 ml.

Yet a further aspect of the invention is a method for determining an effective dose of a composition comprising one or more agents for treating erectile dysfunction in a male. The method comprises the steps of: a) assessing the general, physical and psychological condition of the male; b) administering a test dose guided by step a); c) observing at least one erection characteristic of the male subsequent to administration of the test dose; and d) adjusting the composition to provide an effective erection.

The method can further include measurement of blood flow to the arteries of the penis. Measurement of blood flow can be taken prior to and after administration of the test dose. The method can also include determining the sensitivity and condition of the nerves of the penis. The method can further include determining the sensitivity of the glans of the penis.

The method can be used to determine an effective dose of a composition that includes papaverine, PGE1, phentolamine and atropine. Effective doses can be determined for preferred embodiments of compositions that include amounts of PGE1, papaverine, phentolamine and atropine in the range of 3-12 µg, 5-15 mg, 1-5 mg, and 0.05-0.15 mg in a volume of 1 ml.

Also included in the invention is a method of providing treatment of male sexual dysfunction to a population of male subjects. The method can include the steps of: a) assessing the general, physical and psychological condition of each subject; b) formulating a test dose of a pharmaceutical composition of one or more agents in an amount effective to cause the subject to sustain an erection, guided by step a); c) administering a test dose; d) observing at least one erection characteristic of the subject subsequent to administration of the test dose; e) optionally altering the composition and repeating steps c) and d) until an effective erection is obtained; and f) prescribing for each subject a treatment formulated according to steps a)-e).

Treatment according to the method can be administration of the composition by ICP. The treatment can be self-administered by the subject. The method can further include a prescribed treatment including a kit that can include a pharmaceutical composition of one or more agents in an amount effective to cause the subject to sustain an erection, an apparatus for self-injection of the penis, and instructions for use.

Also included in the invention are kits including a pharmaceutical composition of one or more agents in an amount effective to cause a male subject to sustain an erection, an apparatus for self-injection of the penis, and instructions for use. The composition in the kit can include at least one vasodilator selected from the group consisting of papaverine, PGE1, phentolamine, and atropine. The instructions for use can include an animated videotape.

BRIEF DESCRIPTION OF THE DRAWINGS

The invention is pointed out with particularity in the appended claims. The above and further advantages of this invention may be better understood by referring to the following description, taken in conjunction with the accompanying drawings, in which:

FIG. 1 is graphic showing criteria used to determine a test dosage.

FIG. 2 is a graphic showing criteria used to determine a prescribed dosage.

DETAILED DESCRIPTION

The invention provides a method of treating sexual dysfunction in a male mammal. A pharmaceutical composition of one or more agents is administered by ICP in an amount effective to cause the male to sustain an erection. The method includes an assessment of the general, physical and psychological condition of the male. A test dose of a pharmaceutical composition is formulated, guided by information obtained in the assessment step. A test dose of the formulated composition is administered to the subject by ICP. The erection characteristics of the male are observed following administration of the test dose. The composition may be subsequently adjusted to provide an effective erection.

The method is suitable for use in any male mammal capable of sustaining an erection. The sexual dysfunction can include erectile dysfunction (ED) and premature ejaculation (PE). The sexual dysfunction can be of physical or psychological origin. The origin of the physical component can be either neurogenic, i.e., caused by nerve damage, or vasculogenic, i.e., caused by arterial damage. It is contemplated that subjects having sexual dysfunction of psychogenic origin may be benefited by the treatment because the confidence built up in having a satisfactory erection will eliminate future performance fears.

Pharmaceutical Compositions

The method includes administration of a pharmaceutical composition of one or more agents effective to cause a male to sustain an erection. The compositions of the invention can be admixtures of one or more of agents known to produce an erection in a male subject. Any agent known to produce an erection in a male subject can be used. In preferred embodiments, the agent can be a vasodilator or a combination of vasodilators shown to be effective for treatment of erectile dysfunction.

Any vasodilator suitable for the purpose of producing an erection can be used. Many agents, with differing mechanisms of action, are known as vasodilators. In preferred embodiments, suitable vasodilators can include prostaglandin E1 (PGE1), phentolamine, atropine and papaverine. Phentolamine is known as an antihypertensive agent. It is a competitive, nonspecific alpha-adrenoceptor antagonist that works by direct action on smooth muscle to cause relaxation. Atropine is an anti-muscarinic anti-cholinergic drug believed to stimulate the release of nitrous oxide from the sinusoidal endothelium of corporal tissue. The prostaglandins are a family of important regulatory hormone-like compounds found mainly in the genital organs. PGE1 is a vasodilator that acts as a potent smooth muscle relaxant by functioning as an alpha adrenergic blocker, as well as by elevating intracellular levels of cGMP. Papaverine acts as a smooth muscle relaxant by inhibiting cyclic mononucleotide phosphodiesterases, leading to increased cAMP and cGMP concentrations. It is known to block voltage dependent calcium channels. Other vasodilators and agents suitable for the purpose, acting by these or other mechanisms, may be determined and used alone or in combination using the disclosed methods.

The compositions used in the methods of the invention can be provided, e.g., to a clinic, in several base formulations that are further tailored to the individual needs of the patient by the methods described herein. The base formulations can include a single agent or a combination of agents. Any number of agents suitable for the purpose can be used in the combination. In formulations containing a combination of agents, the proportions of the particular agents within the combination can be varied. For ease of use by the practitioner, each base formulation can be designated by an identifier code number. Any number of base formulations can be provided, and any suitable means of identification can be used.

As an example of the method, six base formulations can be provided, designated by identifier codes such as F0, F1, F2, F3, F4, F5 and F6. Formulation F0 can be, for example, a one-drug formulation, containing, e.g., PGE1 alone. Formulations F1-F6 can all contain combinations of vasodilators, e.g., PGE1, phentolamine, atropine and papaverine. In preferred embodiments, the formulations can include combinations containing all four of these drugs, or only three, i.e., phentolamine, atropine and papaverine.

Each combination drug formulation can further be provided in multiple formulations that vary according to the relative proportions of the drugs within them. Availability of such premixed formulations provides a convenient means of prescribing amounts of the combined agents tailored in proportion to the particular needs of the patient. As an example, F1 can contain a mixture of stock solutions of PGE1, papaverine, phentolamine and atropine, combined by volume in the ratios of 15:45:25:15, respectively. F2 can contain the same four drugs, combined in the ratios of 30:35:20:15. F3 can contain these drugs in the ratios of 60:20:25:5. F5 can contain the four vasodilators in the same ratios as F2, but at double their concentrations. F6 can be a diluted version of F2, containing the same four vasodilators, e.g., at half strength. A three-drug formulation can be included, designated, e.g., F4, that contains a combination of three vasodilators, e.g., papaverine, phentolamine and atropine. In preferred embodiments, these three drugs can be combined in the ratios of 40:40:20 by volume. Further details of methods of preparing three- and four-drug formulations found to be effective in the practice of the invention are provided in the examples below.

All formulations can be provided in a suitable pharmaceutical vehicle. The components of the composition will preferably be in a vehicle that is physiologically compatible and that will allow the dissolution or suspension of the composition components. The components are preferably in an aqueous based pharmaceutically acceptable solution.

Suitable pharmaceutical vehicles are well known to those skilled in the art and are described in several manuals, including Remington's Pharmaceutical Sciences, 15th edition. When PGE1 is used without the other components, it is not stable in water at room temperature although for practical purposes it may be at room temperature for short periods of time. Similarly, formulations containing PGE1, papaverine, phentolamine and atropine, should be kept under refrigeration. A combination of papaverine, phentolamine and atropine can be stored without refrigeration.

Assessment of Sexual Dysfunction

The invention includes a method of treating sexual dysfunction in a male mammal that includes ICP administration of a pharmaceutical composition of one or more agents in an amount effective to cause the male to sustain an erection. It has been shown that the most effective combinations of agents can be determined with the least number of test doses, and with minimization of unwanted side effects of incorrectly prescribed medication, by the disclosed methods.

In a first step in the method of treatment, subjects are assessed to determine the nature of their sexual dysfunction. In the practice of the invention with human males, patient health history and the nature of the sexual problem are determined by interviewing the subject. It is important that the medical history be thorough and detailed in order alert the practitioner to any possible medical conditions that should be addressed. Information obtained from the history can include significant medical conditions, e.g. diabetes, medications currently taken, use of tobacco or alcohol and drug abuse if any, as well as age and an overall assessment of health by the patient.

The subject is further asked to a respond to questions regarding a number of clinical indicators. The clinical indicators can include but are not limited to: the nature of the erection the patient is capable of sustaining during sexual encounters and by masturbation, the duration of the period of erectile dysfunction, the absence or presence and nature of the patient's morning erections, the percentage frequency of erections sufficient for vaginal penetration, the response of the patient to sildenafil, if known, and the occurrence, if any, of premature ejaculation.

Formulation of Test Dose

The method includes a step of formulating a test dose of a pharmaceutical composition effective to cause the male to sustain an erection. Formulation of a diagnostic test dose of medication is guided by a compilation of clinical indicators. The clinical indicators can be compiled such that patients can be assigned to one of several initial treatment groups. In some embodiments of the method, the clinical indicators can be displayed in the form of a chart that correlates the compiled clinical information with the selection of a test dose formulation.

Any number of treatment groups can be designated, and any combination of appropriate clinical indicators may be used. Determination of treatment group categories and selection of appropriate formulations is based on clinical experience with a population of subjects who fall into categories having particular combinations of indicators, including age groups. Compilation of such information from a population can be used to predict the appropriate effective combination and dosage of agents to be used in a customized formulation for a patient who falls into a particular treatment group.

In an example of this method, it has been determined that the longer the patient has had the erectile problem, the more likely it will be that he will require a stronger formula or a greater dose of formulations described herein. The rigidity and duration of a patient's erections is also informative: the less rigid and the less able to penetrate, the more advanced the problem, indicating the need to provide a stronger formula or a greater dose. If the patient has tried sildenafil, his response to this medication is instructional: failure to respond to sildenafil indicates a greater likelihood of requiring a higher dose or a stronger formula. Conversely, a good response to this drug tends to imply that a weaker dosage will be appropriate. The choice of test dosage can also be guided according to the nature of the patient's problem. For example, a patient seeking help for erectile dysfunction (ED) may require a higher dose or a stronger formula than a patient with a problem of premature ejaculation (PE). The quality of a patient's morning erections can also provide information about the nature of the problem. The stronger a patient's erections are in the mornings, the more likely it is that the problem is of psychological origin and hence can be resolved using a weaker dose. Age has also found to be a factor in patient response to a particular formulation: the older the patient, the less responsive he is to the medication. Therefore, a greater dose or stronger formulation is generally required with increasing patient age.

An example of the method for formulating a test dose is shown in Chart 1 (FIG. 1). In this example, compiled clinical indicators were used to define four categories of male erectile dysfunction (designated Groups 1-4), for purposes of choosing a test dose of medication. The choice of formulation of the test dose was further varied within each of the four groups according to the age of the patient.

Assessment of the subject can include the use of physical diagnostic tests which may further assist in determining the formulation of the test dose. A useful diagnostic test is a measurement of blood flow through the penis. Any method suitable for performing this measurement can be utilized. In a preferred embodiment of the method, this test is performed using an ecodoppler. This test is used to determine if there has been any reduction in blood flow through the patient's cavernosal arteries. Blood flow can be used as a parameter for categorizing patients into diagnostic test groups. As an example, blood flow values may be divided into four groups, as shown in the chart in FIG. 1, e.g., with ranges of blood flows correlated with groupings, such as Group 1, 20 cm/s; Group 2, 15-20 cm/s; Group 3, 10-15 cm/s; Group 4, <10 cm/s.

A further physical diagnostic test that may be used is measurement of the sensitivity of the nerve system to the head of the penis. Any method suitable for performing this measurement can be used. A preferred method to perform this test is biothesiometry. Biothesiometry is used to determine if there is any neuropathy (nerve damage). Nerve damage can cause ED of neurogenic origin. This test is used to determine the degree if any of peripheral neuropathy or damage to the nerves that cause the cavernosal arteries to dilate and allow blood to flow into the penis provoking an erection. Biothesiometry is also used to determine how strong the physical component of PE is, by determining the degree of hypersensitivity of the glans or head of the penis. The greater the sensitivity, the more likely it is that the PE is physical in nature (low ejaculatory threshold). As seen in the example shown in FIG. 1, if the results of nerve testing indicate that a patient has a strong neurogenic component, but a weak vascular component to his ED, this information can be helpful in assignment of the patient to a particular group.

Based upon the combination of information gained from the interview and physical testing, an appropriate formulation is selected to be used in a test dose of medication. As described above, the amount and composition is based on the determined clinical indicators, as well as the age of the patient. In an embodiment using a chart for compilation of clinical indicators and suggested dosages, for example as shown in FIG. 1, the formulation and volume of the composition to be tested can be determined as indicated in the lower portion of the chart.

Administration of Test Dose

The method includes a step of administering by a test dose of a pharmaceutical composition effective to cause a male to sustain an erection. The test dose of the medication is preferably administered intracavernosally, i.e., by ICP, because this method delivers the medication to its precise site of action (i.e., the corpus cavernosum), minimizing unwanted side effects caused by systemic administration of drugs such as centrally acting vasodilators.

The method further includes a step of observing one or more characteristics of the erection in order to evaluate the quality of the erection that results from administration of the test dose. Any method suitable for evaluating the quality of the erection can be used. Suitable methods can include visual inspection, measurement of erection angle, palpation, timing of initiation and duration of erection following administration of the agent, ability to penetrate, ability to ejaculate, presence or absence of discomfort, response to erotic stimulus, and time required for return of flaccidity. Yet another suitable test is to measure the change in blood flow to the penis following administration of the test dose. Once the response to the test formulation has been determined, an adjustment can be made depending on this response. The dosage can be either reduced or increased depending on the quality of the erection that the patient has achieved using the diagnostic dose. In some embodiments, directions for adjustment of the dosage can be compiled into a table, as well as directions for prescribing a dosage based on the results of the diagnostic test step. An example of such a table is shown in FIG. 2.

In another aspect, the invention includes a method of determining an effective dose of a composition including one or more agents for treating erectile dysfunction in a male. The method includes the steps of a) assessing the general, physical, and psychological condition of the male; b) administering a test dose guided by the assessment performed in step a); observing at least one erection characteristic of the male after administration of the test dose; and d) adjusting the composition to provide an effective erection.

Treatment of Sexual Dysfunction in a Population

The invention further provides a method of providing treatment of male sexual dysfunction to a population of male subjects. The method includes the steps of: a) assessing the general, physical and psychological condition of each subject; b) formulating a test dose of a pharmaceutical composition of one or more agents in an amount effective to cause said subject to sustain an erection, guided by step a); c) administering a test dose; d) observing the erection characteristics of the subject subsequent to administration of the test dose; e) optionally altering the composition and repeating steps c) and d) until an effective erection is obtained; and f) prescribing for each said subject a treatment formulated according to steps a)-e). In preferred embodiments of the method, the treatment is administration of the composition by ICP. The treatment can be self-administered by the subject. The treatment method can include prescribing a kit containing a pharmaceutical composition of one or more agents in an amount effective to cause the subject to sustain an erection, an apparatus for self-injection of the penis, and instructions for use.

Kits

The invention further includes kits containing the prescribed composition and an apparatus used by the patient to administer the composition. In a preferred embodiment, the apparatus can be a specialized syringe with an automatic injector. Such devices are known in the art of urology. The apparatus for self-injection can include an applicator into which a preloaded syringe is placed. The applicator can be designed such that with the press of a button, a fine needle is injected to the correct depth into the corpus cavernosum. This type of apparatus is advantageous both for its ability to regulate the depth of the injection, and for facilitating self-use by the subject. Also contemplated are home and travel kits that include individualized dosages of the customized composition, an apparatus for self-injection of the composition, and instructions for use.

In some embodiments, instructions included in the kit can be in the form of an animated videotape. The animations in the videotape can illustrate the correct method of holding the penis and the applicator during injection, the range of possible sites for injection and the procedures for dispensing medication from the injector and distributing the medication by massage of the penis after injection. The videotape can also include reminders to the patient about storage of the medication and information about how to obtain medical support regarding use of the medication. Inclusion of a videotape in the kit provides a useful and reassuring review for the patient of procedures discussed and demonstrated during visits to the clinic.

There is virtually no discomfort when the patient injects the composition because the central part of the penis is relatively insensitive in contrast to the penis head, which is a sensitive area. The central shaft is composed of spongy tissue and injection into this area places the solution into the cavernosa. The patient may have some initial trepidation concerning the first self-injection. This is readily overcome by instructions and practice in the physician's office and a complete instruction sheet or videotape accompanying the dosage kits. Fear of pain is dispelled, and in fact some patients need to be warned that a lack of pain is not an indication that the drug did not reach the targeted area.

In practice, the patient simply injects the proper dose into the dose into the proximal third of the penis. Typically, a rapid response is obtained within 5 minutes. The duration of the erection is, on average, 25 to 45 minutes. The penis remains erect during this period regardless of ejaculation, in contrast to agents such as sildenafil, with which the penis becomes flaccid after ejaculation. Erotic stimulation is not required with this treatment, as it is with sildenafil.

EXAMPLES

Example 1

Preparation of Formulations for Erectile Dysfunction

This example describes the preparation of agents found to be effective and convenient for use in the methods of the invention, with designations corresponding to those indicated in the charts in FIGS. 1 and 2. In this example, six base formulations of the compositions were prepared and designated by code numbers F0, F1, F2, F3, F4, F5 and F6. Formulation F0 was prepared to include PGE1 only, at a concentration of 10 µg/ml. Formulations designated F1, F2, F3, F5 and F6 all contained combinations of four vasodilators, i.e., PGE1, phentolamine, atropine and papaverine, but in differing proportions or concentrations. F1 contained a mixture of solutions of PGE1, papaverine, phentolamine and atropine, combined in the respective ratios of 15:45:25:15 by volume. The final formulations were achieved conveniently by combining mixtures of stock solutions in varying volume proportions. For specifically, a solution of PGE1 was prepared in saline at a concentration of 20 µg/ml. A solution of papaverine was prepared in a hydrochloride vehicle at a concentration of 30 mg/ml. Phentolamine was prepared in a hydrochloride solution at a concentration of 10 mg/ml, and atropine was prepared in a sulphate solution at a concentration of 1 mg/ml. Using solutions thus prepared, formulation F1, having the ratio of 15:45:25:15, was prepared by mixing 15 mls of the PGE1 (20 µg/ml), 45 mls of papaverine (30 mg/ml), 25 mls of phentolamine(10 mg/ml) and 15 mls of atropine (1 mg/ml), for a total volume of 100 mls. Accordingly, final concentrations of the four vasodilators in formulation F1 were PGE1: 3 µg/ml; papaverine: 13.5 mg/ml; phentolamine: 2.5 mg/ml; and atropine: 0.15 mg/ml.

Formulation F2 contained the same four drugs, prepared from stock solutions at the concentrations stated above, but combined in the ratios of 30:35:20:15 by volume. Therefore the resulting formulation contained PGE1, papaverine, phentolamine, and atropine at the respective final concentrations of 6 µg/ml, 10.5 mg/ml, 2.0 mg/ml and 0.15 mg/ml. F3 contained the same four drugs combined in the ratios of 60:20:25:5, to yield a composition containing PGE1, papaverine, phentolamine, and atropine at the respective final concentrations of 12 µg/ml, 6.0 mg/ml, 2.5 mg/ml and 0.05 mg/ml. F5 contained the four vasodilators in the same ratios as F2, but at double their concentrations. F6 was prepared by combining the same four vasodilators in the ratios for F2, but at half strength.

Formulation F4 contained a combination of only three vasodilators, i.e., papaverine, phentolamine and atropine in the ratios of 40:40:20 by volume, using stock solutions prepared as described above. Final concentrations of papaverine, phentolamine and atropine solutions in formulation F4 were therefore 12.0 mg/ml, 4 mg/ml, and 0.2 mg/ml, respectively.

In general, the above described formulations contained amounts of PGE1, papaverine, phentolamine, and atropine, in the range of about 8-35 μM, 14-45 mM, 2-15 mM and 0.05-0.15 mM, respectively.

Example 2

Determination of Test and Effective Doses of Formulations

This example describes how test doses and adjusted doses of formulations designated by identifiers F0-F6, described herein, can be determined by a practitioner, by reference to guidelines provided in chart form. In the charts shown in this example (FIGS. 1 and 2), predictive clinical indicators were compiled into four patient groups having the observed combination of parameters. Correlations were made with dosages found to be effective for each of these groups. Referring to FIG. 1, it can be seen that to determine an appropriate test dose for a 30-year-old classified in Group 3, a suggested test dose is 14 units (0.14 ml) of formulation F2. By contrast, a 60-70 year old subject in the same group could initially be administered 36 units (0.36 ml) of formulation F2. In this example, all dosage volumes are shown in units, where 10 units=0.1 ml.

Referring now to Chart 2, (FIG. 2), if the resulting erection is 70-80% in response to the test dose, the prescribed dose is increased by 25-50% of the volume used for the test dose (e.g., by 0.09-0.18 ml of F2 for a 60-70 year old subject with erectile dysfunction, ED).

Chart 2 provides additional guidance for selection of an effective dosage following administration of the test dose. As seen in the notes below the chart, formulations can be modified for the rare patients who experience a priapism or prolonged erection (3-6 hours) following administration of the test dose. If the problem resolves with conservative treatment or with the administration of an antidote such as epinephrine, the test formulation is changed from F2 to F1, then to F0 if necessary. If the patient experiences a priapism that requires draining, the formulation is changed to F0 (containing PGE1 alone), starting at 20 units.

Also shown in Chart 2 is direction for a practitioner whose patient experiences no response with the maximum dosage (100 units), e.g., of formulation F2. In this case, the patient can be tested with 100 units of F5, which contains the same ingredients as F2 but at double their respective concentrations.

The prescribed dosage table (Chart 2) also contains columns to separate patients with erectile dysfunction (ED) and those with premature ejaculation (PE). The reason for this separation is that patients with PE tend to require a more conservative adjustment than those with ED.

OTHER EMBODIMENTS

While the methods and compositions of this invention have been described in terms of preferred embodiments, it will be apparent to those of skill in the art that variations may be applied to the methods and compositions, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of treating premature ejaculation in a male mammal via ICP administration of a pharmaceutical composition of one or more erection-producing agents in an amount effective to cause said male to sustain an erection, said method comprising the steps of:
   a) assessing the general, physical and psychological condition of the male;
   b) formulating a test dose of said composition guided by step (a);
   c) administering the test dose;
   d) observing at least one erection characteristic of the male subsequent to administration of the test dose; and
   e) adjusting the composition according to the observations in step (d) to provide an effective erection, wherein the composition comprises papaverine, phentolamine, and atropine.

2. The method of claim 1 wherein assessing the physical condition in step (a) further comprises measuring blood flow to the arteries of the penis.

3. The method of claim 1 wherein assessing the physical condition in step (a) further comprises determining the sensitivity and condition of the nerves of the penis.

4. The method of claim 1 wherein the composition comprises a vasodilator.

5. The method of claim 1 wherein the composition further comprises PGE1.

6. The method of claim 5 wherein the composition comprises amounts of PGE1, papaverine, phentolamine, and atropine, in the range of about 8-35 μM, 14-45 mM, 2-15 mM and 0.05-0.15 mM, respectively.

7. The method of claim 5 wherein the composition comprises an amount of PGE1, papaverine, phentolamine, and atropine of about 3 μg, 13.5 mg, 2.5 mg, and 0.15 mg, respectively, in a volume of 1 ml.

8. The method of claim 5 wherein the composition comprises an amount of PGE1, papaverine, phentolamine, and atropine of about 6 μg, 10.5 mg, 2 mg, and 0.15 mg, respectively, in a volume of 1 ml.

9. The method of claim 5 wherein the composition comprises an amount of PGE1, papaverine, phentolamine, and atropine of about 12 μg, 6 mg, 2.5 mg, and 0.05 mg, respectively, in a volume of 1 ml.

10. The method of claim 5 wherein the composition comprises an amount of PGE1, papaverine, phentolamine, and atropine of about 12 μg, 21 mg, 4 mg, and 0.3 mg, respectively, in a volume of 1 ml.

11. The method of claim 5 wherein the composition comprises an amount of PGE1, papaverine, phentolamine, and atropine of about 3 μg, 5 mg, 1 mg, and 0.8 mg, respectively, in a volume of 1 ml.

12. The method of claim 1 wherein the composition comprises an amount of papaverine, phentolamine, and atropine of about 12 μg, 4 mg, and 0.2 mg, respectively, in a volume of 1 ml.

13. The method of claim 1 wherein the composition is in a pharmaceutically acceptable vehicle.

14. The method of claim 13 wherein the pharmaceutical vehicle further comprises a stabilizer.

15. The method of claim 1 wherein the effective amount of the composition is contained in a volume from about 0.01 ml to about 2.0 ml.

16. A method for determining an effective dose of a composition comprising one or more erection-producing agents for treating premature ejaculation in a male, the method comprising the steps of:
  a) assessing the general, physical and psychological condition of the male;
  b) administering a test dose guided by step (a);
  c) observing at least one erection characteristic of the male subsequent to administration of the test dose; and
  d) adjusting the composition according to the observations in step (d) to provide an effective erection, wherein the composition comprises papaverine, phentolamine, and atropine.

17. The method of claim 16, further comprising measuring blood flow to the arteries of the penis.

18. The method of claim 16, further comprising measuring blood flow to the arteries of the penis prior to and after the test dose.

19. The method of claim 16, further comprising determining the sensitivity and condition of the nerves of the penis.

20. The method of claim 16, further comprising determining the sensitivity of the glans of the penis.

21. The method of claim 16, wherein the composition further comprises PGE1.

22. The method of claim 21, wherein the composition comprises amounts of papaverine, PGE1, phentolamine, and atropine in the range of about 3-12 µg, 5-15 mg, 1-5 mg, and 0.05-0.15 mg, respectively, in a volume of 1 ml.

23. A method of providing treatment of premature ejaculation to a population of male subjects, said method comprising the steps of:
  a) assessing the general, physical and psychological condition of each subject;
  b) formulating a test dose of a pharmaceutical composition of one or more erection-producing agents in an amount effective to cause said subject to sustain an erection, guided by step (a);
  c) administering the test dose;
  d) observing at least one erection characteristic of the subject subsequent to administration of the test dose;
  e) optionally altering the composition according to the observations in step (d) and repeating steps (c) and (d) until an effective erection is obtained, wherein the composition comprises papaverine, phentolamine, and atropine; and
  f) prescribing for each said subject a treatment formulated according to steps (a)-(e).

24. The method of claim 23 wherein the treatment is administration of said composition by ICP.

25. The method of claim 23 wherein the treatment is self-administered by the subject.

26. The method of claim 23 wherein the prescribed treatment comprises a kit comprising a pharmaceutical composition of one or more erection-producing agents in an amount effective to cause said subject to sustain an erection, an apparatus for self-injection of the penis, and instructions for use.

27. The method of claim 1, wherein the composition comprises papaverine, phentolamine, and atropine in a ratio of 40:40:20 by volume, respectively.

28. The method of claim 5, wherein the composition comprises PGE1, papaverine, phentolamine, and atropine in a ratio of 15:45:25:15 by volume, respectively.

29. The method of claim 5, wherein the composition comprises PGE1, papaverine, phentolamine, and atropine in a ratio of 30:35:20:15 by volume, respectively.

30. The method of claim 5, wherein the composition comprises PGE1, papaverine, phentolamine, and atropine in a ratio of 60:20:25:5 by volume, respectively.

31. A method of treating sexual dysfunction in a male mammal via ICP administration of a pharmaceutical composition of one or more erection-producing agents in an amount effective to cause said male to sustain an erection, said method comprising the steps of:
  a) assessing the general, physical and psychological condition of the male including assessing a number of factors, said factors including a blood flow, an erection percentage, an incidence of premature ejaculation, an incidence of neurogenic erectile dysfunction, an incidence of psychogenic erectile dysfunction, a quality of sustainability of erection, an incidence of morning erection, a duration of dysfunction, a frequency of penetration, and an age;
  b) formulating a test dose of said composition based on a particular combination of the number of factors by step (a);
  c) administering the test dose;
  d) observing at least one erection characteristic of the male subsequent to administration of the test dose; and
  e) adjusting the composition according to the observations in step (d) to provide an effective erection, wherein the composition comprises papaverine, phentolamine, and atropine, wherein the sexual dysfunction is premature ejaculation.

32. The method of claim 31 wherein, when the blood flow is greater than 20 cm/s or the erection percentage is 100% or the incidence of premature ejaculation is positive, or the incidence of neurogenic erectile dysfunction is positive or the incidence of psychogenic erectile dysfunction is positive, the test dose comprises PGE1, papaverine, phentolamine and atropine, in the ratios of 15:45:25:15, respectively.

33. The method of claim 31 wherein, when the blood flow is 15-20 cm/s or the erection percentage is greater than 70-75% or the sustainability of erection of poor or morning erection is positive or dysfunction is less than 12 months or the frequency of penetration is greater than 50% of the time, and the age is between 20-50, the test dose comprises PGE1, papaverine, phentolamine and atropine, in the ratios of 15:45:25:15, respectively.

34. The method of claim 31 wherein, when the blood flow is 15-20 cm/s or the erection percentage is greater than 70-75% or the sustainability of erection of poor or morning erection is positive or dysfunction is less than 12 months or the frequency of penetration is greater than 50% of the time, and the age is over 50, and the test dose comprises PGE1, papaverine, phentolamine and atropine, in the ratios of 30:35:20:15, respectively.

35. The method of claim 31 wherein, when the blood flow is 10-15 cm/s or the erection percentage is less than 65% or the sustainability of erection is poor or morning erection is negative or dysfunction is between 12-24 months or the frequency of penetration is about 50% of the time, the test dose comprises PGE 1, papaverine, phentolamine and atropine, in the ratios of 30:35:20:15, respectively.

36. The method of claim 31 wherein, when the blood flow is less than 10 cm/s or the erection percentage is less than 50% or the sustainability of erection is poor or morning erection is negative or dysfunction is more than 24 months or no possibility of penetration, the test dose comprises PGE1, papaverine, phentolamine and atropine, in the ratios of 30:35:20:15, respectively.

* * * * *